United States Patent [19]

Fedorov et al.

[11] Patent Number: 4,799,478

[45] Date of Patent: Jan. 24, 1989

[54] DEVICE FOR COAGULATION OF BIOLOGICAL TISSUES

[76] Inventors: Svyatoslav N. Fedorov, ulitsa Dostoevskogo, 21, kv. 32, Moscow; Sergei V. Krutov, poselok Klyazma, ulitsa Krylovskaya, 6, Moskovskaya oblast; Sergei A. Soloviev, ulitsa Podolskava, 9, kv. 247, Moscow; Olga G. Alexandrova, ulitsa 1812 goda, 1, kv. 139, Moscow; Nadezhda K. Korshunova, 3 Mikhalkovsky pereulok, 8, korpus 2, kv. 40, Moscow, all of U.S.S.R.

[21] Appl. No.: 937,317

[22] Filed: Dec. 3, 1986

[30] Foreign Application Priority Data

Dec. 16, 1985 [SU] U.S.S.R. ............................... 3990084

[51] Int. Cl.$^4$ ............................................. A61B 17/38
[52] U.S. Cl. ................................................. 128/303.1
[58] Field of Search ........... 128/303.1, 303.13, 303.14, 128/303.17, 303.18

[56] References Cited

U.S. PATENT DOCUMENTS 3,884,237  5/1975  O'Malley et al. ............... 128/303.14

FOREIGN PATENT DOCUMENTS 2351748  4/1975  Fed. Rep. of Germany ......................... 128/303.18
365994  5/1973  U.S.S.R. ......................... 128/303.17

OTHER PUBLICATIONS

Hanz Gender Catelogue, FRG, Heidelberg, 1981, p. 107.

*Primary Examiner*—Lee S. Cohen
*Attorney, Agent, or Firm*—Ladas & Parry

[57] ABSTRACT

Device for coagulation of biological tissues, preferably the eye cornea has a casing accommodating a hollow rod having one end thereof supporting a heating element secured thereto and facing towards the eye cornea and having the other end thereof operatively connected, by means of a connecting member, with a shaft of an electric motor accommodated in the casing on which a stop for limiting movement of the hollow rod is mounted, the stop being in the form of a hollow fine adjustment screw having a dial gage in the form of a scale provided on the head of the hollow fine adjustment screw and an indicator mark made on the casing. A stop for limiting movement of the heating element is secured to a working end of the casing facing towards the eye cornea, the stop being in the form of a cantilever having a free end thereof supporting a rigid ring secured thereto coaxially with the heating element. The device has a unit for automatically controlling the heating temperature and treatment time having one output thereof connected to a power supply unit having its outputs connected, through the automatic control, unit, to the heating element and electric motor.

5 Claims, 3 Drawing Sheets

DEVICE FOR COAGULATION OF BIOLOGICAL TISSUES

FIELD OF THE ART

The invention relates to the field of medicine and, more particularly, to equipment for ophthalmological operations, namely to devices for coagulation of biological tissues.

INDUSTRIAL FIELD TO BE APPLIED

The invention may be used in devices for coagulation of eye tissues, e.g. cornea, in order to change the curvature thereof. Such devices may also be employed for coagulation of biological tissues in other fields of medicine, e.g. for the cauterization of hair bulbs and connective tissues during cosmetic and plastic operations.

BACKGROUND OF THE INVENTION

Known in the art is a device for coagulation of eye tissues (cf., HANZ GENDER catalogue, FRG, Heidelburg, publ. 1981, p. 107) comprising a casing made of metal (e.g. aluminium) to which a heating element in the form of a rigid metal loop is secured by means of microjacks. The heating element is connected to a power supply unit having a button switch and being in the form of a d.c. source accommodated in the interior space of the casing and is insulated from the casing by means of bushings made of an insulating material. The working end of the heating element to be introduced into the eye tissues protrudes on the side of the working butt end of the casing facing the object of treatment, e.g. the eye cornea.

To carry out local coagulation of eye tissues, the power supply unit is connected to the heating element by pressing the button switch. The heating element is heated by the flowing current. The working end of the heating element is brought into contact with a zone of the cornea. The location of the coagulation zone, coagulation depth and time of treatment of the cornea by the heating element is corrected visually.

However, this known device does not ensure sufficient accuracy because the working end of the heating element cannot be positioned to a given calculated depth corresponding to the coagulation depth at a given point of the cornea. Furthermore, the depth of introduction of the working end is unstable in the course of the operation and entirely depends on the manual skill of the surgeon. The design of the device for coagulation of biological tissues does not ensure precise heat input to the heating element or accurate measurement of the time of treatment of biological tissues of the eye and the depth of introduction of the working end of the heating element. This may be the reason of operational implications in the form of cornea perforation, post operational astigmatism, cornea necrosis in the coagulation zone due to coarse cicatrization and overcauterization of the eye tissues.

SUMMARY OF THE INVENTION

It is an object of the invention to improve the accuracy of ophthalmological operations and reduce operational and post operational implications by making precisely adjustable such eye cornea treatment factors as introduction of the working end of a heating element in the cornea while maintaining a stable depth of introduction during multiple coagulations during one operation.

Means for Solving the Problem

This problem is achieved by that a device for coagulation of biological tissue which is the object of treatment, comprising a casing having a heating element having a working end acting on the biological tissue and protruding outside on the side of a working butt end of the casing, facing the object of treatment, and a power supply unit electrically connected to the heating element, according to the invention, comprises a hollow rod mounted for reciprocation in the casing and having one butt end thereof supporting the heating element rigidly secured thereto and having the other butt end operatively connected, by means of a connecting member, with a shaft of an electric motor accommodated in the casing, which has a first limit stop for limiting the movement of the hollow rod having a dial gage, a second limit stop for limiting the movement of the heating element which is rigidly secured to the casing, while the electric motor and the heating element are connected to the power supply unit via a unit for automatic control of the heating temperature and time of treatment of the biological tissue.

It is desirable that in the device, according to the invention, the first limit stop the limit stop of the heating element be made in the form of a cantilever having one end thereof rigidly secured to the working butt end of the casing and having the other end thereof supporting a rigid ring secured thereto coaxially with the heating element, while the working end of the heating element be made in the form of a conical pointed member.

It is desirable that in the device, according to the invention, the first limit stop the limit stop for the hollow rod be made in the form of a hollow fine adjustment screw mounted coaxially with the shaft of the electric motor in a threaded hole of the casing while the dial gage of the hollow rod with two butt ends be made in the form of a scale provided on the head of the hollow fine adjustment screw and an indicator mark made on the casing, the shaft of the electric motor be made a screw type shaft, the connecting member being made in the form of a cantilever having one end thereof rigidly secured to the end of the hollow rod, while the other end is made in the form of a resilient fork engageable with the shaft of the electric motor.

It is desirable that in the device, according to the invention, the unit for automatic control of the heating temperature and the time of treatment of the biological tissue comprise an RS flip-flop, a turn-on device coupled to an S-input of the RS flip-flop for connecting the device to the power supply unit, a mode switch coupled to the R-input of the RS flip-flop, a pulse generator having its input connected to a noninverting output of the RS flip-flop, a pulse counter having its counting T-input and reset R-input connected to the output of the pulse generator and to an inverting output of the RS flip-flop, respectively, a first OR gate having its inputs connected to a group of outputs of the pulse counter for producing a signal enabling the hollow rod to mode forward, a second OR gate having its inputs connected to several outputs of the first group of outputs of the pulse counter for producing a signal enabling the heating element to be heated, a third OR gate having its inputs connected to a second group of outputs of the pulse counter for producing a signal enabling the hollow rod to move backward, first and second switching circuits having their inputs connected to the outputs of the first and third OR gates and their outputs connected to inputs of a reverse relay, a power cut-in relay having one input thereof connected to one output of the reverse relay and the other input serving to connect the device to the power supply unit, a reverse switch intended to connect the power supply unit to the electric motor and having its inputs connected to a second output of the reverse relay and the output of the power cut-in relay, a heating circuit of the heating element having its input connected to the power supply unit, a third switching circuit having its input connected to the output of the second OR gate and serving to connect the power supply unit to the heating element of the device via the heating circuit, a delay circuit and an AND gate having their inputs connected to the remaining input of the second OR gate and to treatment time signal output of the pulse counter, the output of the delay circuit being connected to the other input of the AND gate whose output is connected to the enabling signal input of the pulse counter having its zero output connected to the mode switch via the turn-on device.

The operation accuracy is achieved by providing the device with the unit for automatically controlling the heating temperature and treatment time, having its outputs connected to the electric motor and heating element which is mounted for reciprocation, and also providing the stop limiting the movement of the heating element which stabilizes the depth, of introduction, and adjustment of the heating element movement by means of the stop for limiting movement of the hollow rod to which the heating element is secured. High accuracy of the operation, i.e. the achievement of the predicted calculated result, is achieved by the precise introduction of the working end of the heating element into the eye cornea. This makes it possible to carry out coagulation of the eye cornea to a specific depth.

The extension of the working end of the heating element can be stabilized at a specific length which is equal to a preset introduction depth. It becomes possible to avoid operation implications in the form of cornea perforation. In addition, the automatic adjustment of the treatment time and heating temperature eliminates overcauterization of the eye cornea which prevents coarse cicatrization and further development of post operational astigmatism and also makes it possible to carry out multiple coagulations during one operation.

These and other objects and advantages of the invention will be apparent from the following detailed description of a specific embodiment thereof and accompanying drawings, in which:

DETAILED DESCRIPTION OF THE INVENTION

Figure 1:
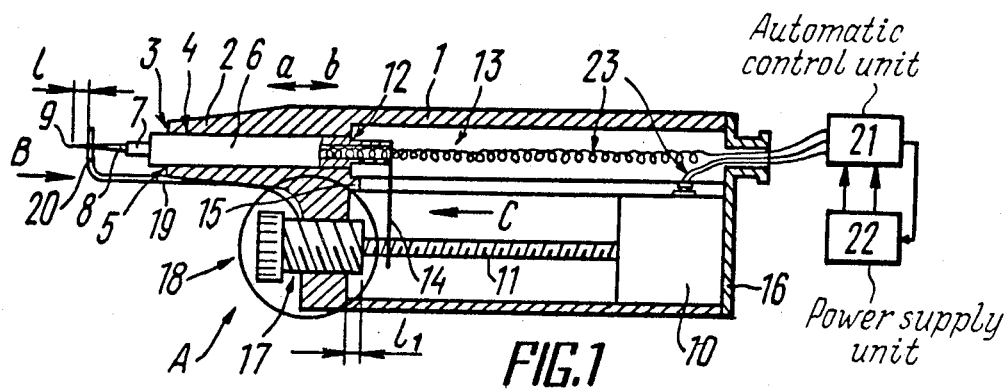
FIG. 1 illustrates a general longitudinal section view of a casing of a device for coagulation of biological tissues, according to the invention.

A device for coagulation of biological tissues comprises a casing 1 (FIG. 1) made of metal, e.g. DURALUMIN (a high strength aluminum alloy containing 4% copper, 0.5% magnesium, 0.25-1% manganese and low percentages of iron and silicon) and featuring a protruding portion 2 having its working butt end 3 facing the object of treatment, i.e. the eye cornea (not shown in FIG. 1). A longitudinal passage 4 having an external outlet 5 at the working butt end 3 is made in the protruding portion 2 of the casing 1. The device is provided with a hollow rod 6 mounted for reciprocation (arrow a-b) in the longitudinal passage 4. A heating element 8 in the form of a rigid loop is secured, by means of a microjack 7, to one end 6' of the hollow rod near the external outlet 5 of the longitudinal passage 4. A working end 9 of the heating element 8 is made in the form of a conical pointed member.

The casing 1 accommodates an electric motor 10 having a shaft 11 whose longitudinal axis is parallel to the longitudinal axis of the hollow rod 6 mounted in the longitudinal passage 4 communicating with an interior space 13 of the casing 1 through its internal outlet 12. The butt end 6" of the hollow rod 6 facing the interior space 13 of the casing 1 is operatively connected, by means of a connecting member 14, with the shaft 11 of the electric motor 10.

The interior space 13 of the casing 1 is divided onto two compartments by a protrusion 15 made on internal walls of the casing 1 and ensuring, together with a cover 16, stationary installation of the electric motor 10 in the casing 1.

The device is also provided with first a stop 17 for limiting the movement of the hollow rod 6, having a dial gage 18, secured to the casing 1 and with a stop for limiting the movement of the heating element 8, which is a cantilever 19 having one end thereof rigidly secured to the working end 3 of the casing 1, the rigid ring 20 being secured to the free end of the cantilever 19 coaxially with the working end 9 of the heating element 8.

The length of the cantilever 19 should be such that when the hollow rod 6 moves forward (arrow "a") the working end 9 might protrude outside with respect to the ring 20 to a length "l" which equals the depth of introduction of the working end 9 into the cornea and which is measured within the range from 0.3 to 0.8 mm. The exact depth "l" is determined for each patient using the results of medical examination and set before the operation by means of the stop 17 for limiting the movement of the hollow rod 6 and the dial gage 18, while the depth stability is ensured by the stop for limiting the movement of the heating element 8, which is rigid ring 20 secured to the cantiilever 19.

The device for coagulation of biological tissues also comprises a unit 21 for automatically controlling the heating temperature and time of treatment of biological tissue. The unit 21 electrically connects the outputs of a power supply unit 22 to the heating element 8 and to the electric motor 10, the outputs of the unit 21 being connected thereto by flexible leads 23.

Figure 2:
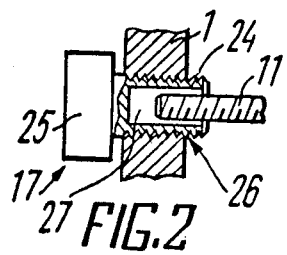
FIG. 2 is an enlarged partial longitudinal section view taken along arrow A of a stop for limiting the movement of a hollow rod, according to the invention.

Referring to FIG. 2, which is a view taken along the arrow A in FIG. 1 of the limit stop 17 of the hollow rod 6 (partial longitudinal section), the stop 17 is a hollow fine adjustment screw 24 having a head 25 and mounted in a threaded hole 26 of the casing 1 coaxially with the shaft 11 which is also of a screw type, the end of the shaft 11 being freely received in an interior space 27 of the fine adjustment screw 24.

Figure 3:
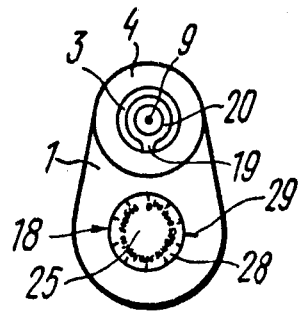
FIG. 3 is an enlarged view taken along arrow B in FIG. 1, according to the invention.

Referring to FIG. 3, the dial gage 18 indicating the movement of the hollow rod 6 is a scale provided on the head 25 of the fine adjustment screw 24 (FIG. 2) in accordance with the thread pitch and an indicator mark 29 (FIG. 3) made on the casing 1 near the threaded hole 26. The dial gage 18 serves to indicate the movement of the fine adjustment screw 24 along the shaft 11 (FIG. 2) in order to limit the movement of the hollow rod 6 (FIG. 1) since the end of the fine adjustment screw 24 (FIG. 2) acts as a stop of the connecting member 14.

The scale 28 (FIG. 3) is circular, and the indicator mark 29 is made on the casing 1. The position of the indicator mark 29 corresponding to the zero point of the scale 28 corresponds to the position of the working end 9 of the heating element 8 (FIG. 1) in flush with the rigid ring 20.

FIG. 3 also shows in detail the arrangement of the working end 9 of the heating element 8 coaxially with the rigid ring 20 of the limit stop of the heating element 8. The diameter of the rigid ring 20 is larger than the diameter of the base of the working end 9 which ensures free passage of the working end 9 when it is being set to a predetermined depth "l".

Figure 4:
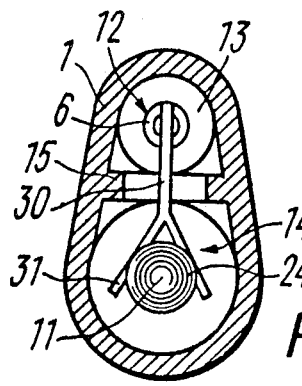
FIG. 4 is an enlarged view taken along arrow C in FIG. 1, according to the invention.

Referring to FIG. 4, which is a view taken along the arrow "C" in FIG. 1, the connecting member 14 may be made, e.g., in the form of a cantilever 30 having one end thereof rigidly connected to the butt end 6" of the hollow rod 6 while the other end is a resilient fork 31 engageable with the shaft 11 which, as has been mentioned above, is of a screw type. The connecting member 14 serves to limit the movement of the hollow rod 6 (FIG. 1) since the end of the fine adjustment screw 24 set at a predetermined immersion depth "l" acts as a stop for the resilient fork 31.

The device for coagulation of biological tissues comprises a unit 21 for automatically controlling the heating temperature and time of treatment of the biological tissue, which is provided with a turn-on device 32 having two groups of contacts which are operatively connected. One contact 33 of the first group is connected to the input of the power supply unit 22, the other contact 34 is connected to the S-input of an RS flip-flop 35 having its noninverting and inverting outputs respectively connected to the input of a pulse generator 36 serving to set the time of movement of the hollow rod 6 (FIG. 1) and to the R-input of the pulse counter 37 (FIG. 5) having its counting T-input connected to the output of the oscillator 36. In the counter 37, the first group of outputs 38, 39, 40, 41 serving to read the signals of forward movement (arrow "a") of the hollow rod 6 (FIG. 1) is connected to inputs of an OR gate 42, the outputs 39, 40, 41 of this group being also connected to inputs of a second OR gate 43, the remaining input thereof being connected to the input of a delay circuit 44, to a first input of an AND gate 45 and coupled to an output 46 of the counter 37 which provides a signal for setting the time of treatment by the heating element 8 (FIG. 1).

Figure 5:
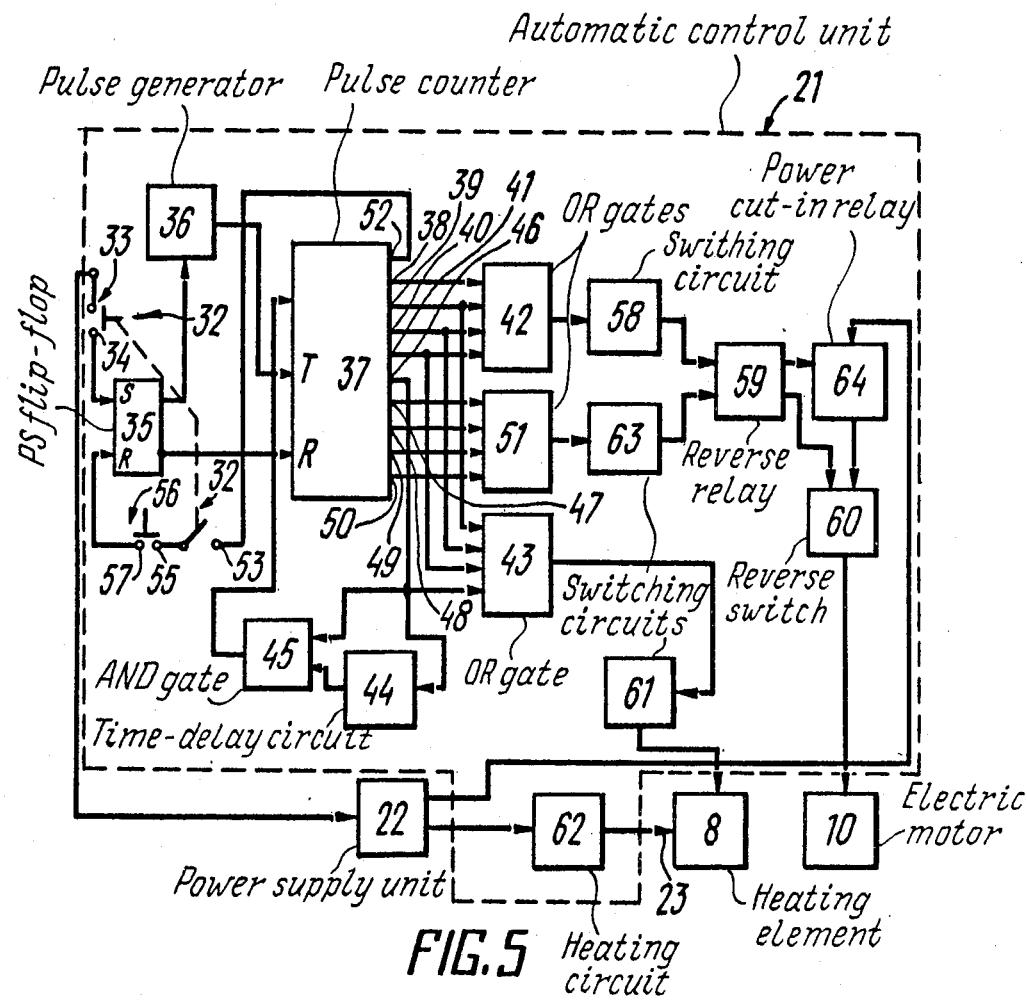
FIG. 5 is a functional diagram of a unit for automatically controlling the heating temperature and the time of treatment of the cornea, according to the invention.

A second group of outputs 47, 48, 49, 50 (FIG. 5) of the counter 37 which provide signals of backward movement (arrow "b") of the hollow rod 6 (FIG. 1) is connected to inputs of a third OR gate 51 (FIG. 5). A zero signal output 52 is connected to one contact 53 of the second group of contacts of the switch member 32, the second contact 54 of this group being connected to one contact 56 of a mode switch 56 having the other contact 57 thereof connected to the R-input of the RS flip-flop 35.

The output and the remaining input of the AND gate 45 are respectively connected to an enabling signal input of the pulse counter 37 and to the output of the delay circuit 44. The output of the first OR gate 42 is connected to the input of a switching circuit 58 producing a signal for forward movement of the hollow rod 6 (FIG. 1). The output of the switching circuit 58 (FIG. 5) is connected to one input of a reverse unit 59 having one output connected to an input of a reverse switch 60 for sending a signal of forward movement of the hollow rod 6 (FIG. 1). The output of the switch 60 is connected to the electric motor 10. The output of the second OR gate 43 is connected to the input of a switching circuit 61 serving to connect the heating element 8 to the power supply unit 22 through a switching heating circuit 62.

The output of the third OR gate 51 is connected, through a switching circuit 63, to the other input of the reverse relay 59 for supplying a signal of backward movement of the hollow rod 6 (FIG. 1). The other output of the relay 59 (FIG. 5) is connected to one input of a power cut-in relay 64 having its output connected to the other input of the reverse switch 60. The other input of the relay 64 is electrically connected to an output of the power supply unit 22 the other output of which is connected to the input of the heating circuit 62 whose output is connected to the heating element 8 by a flexible current lead 23 (FIG. 1) in the form of a twisted spiral.

Figure 6:
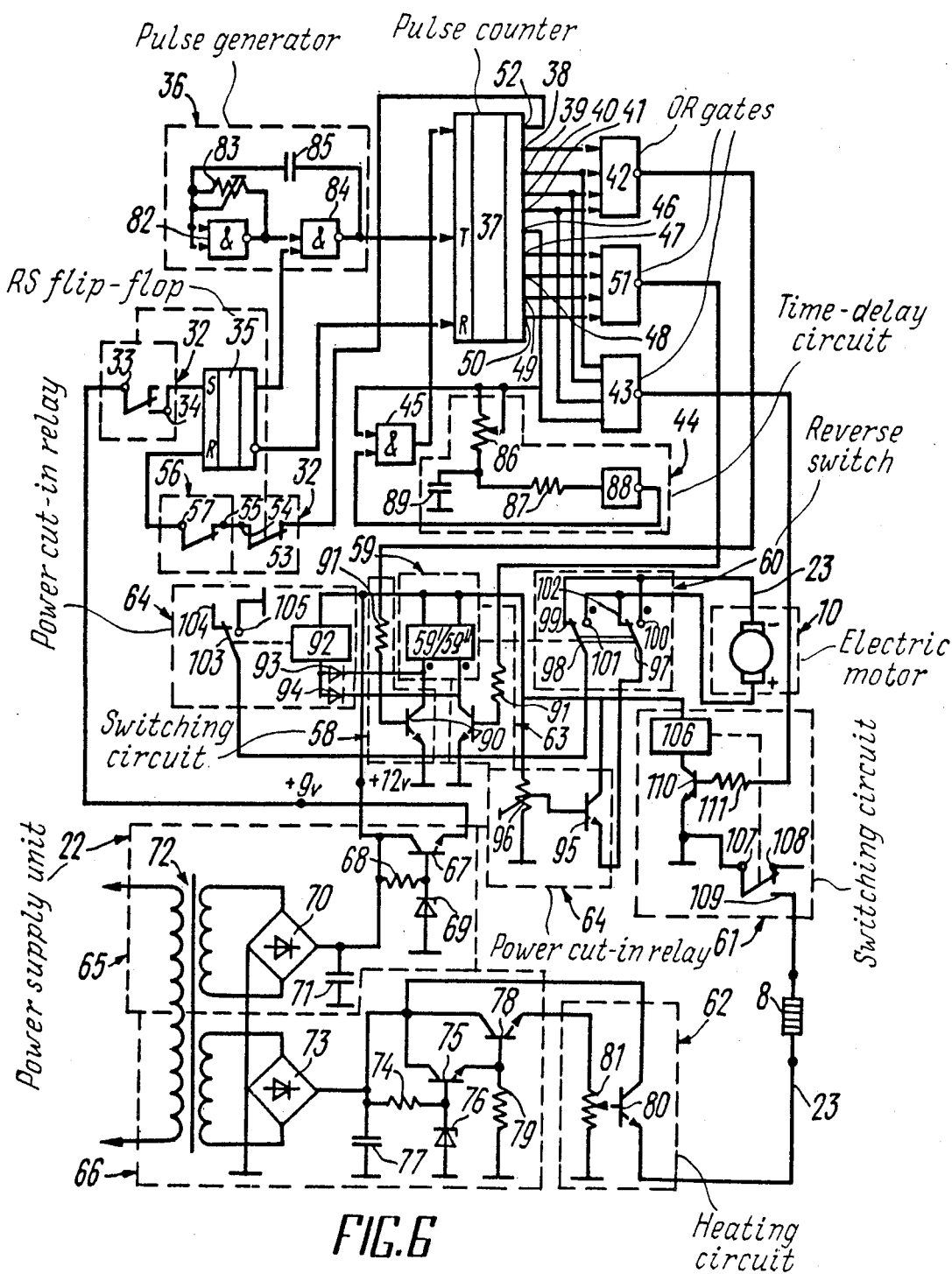
FIG. 6 is an electric circuit diagram of a unit for automatically controlling the heating temperature of the heating element and the time of treatment of the cornea, according to the invention.

FIG. 6 shows a circuit diagram of the device for coagulation of biological tissues. The switch member 32 is made in the form of a pedal having the contact 33 thereof connected to the input of the power supply unit 22 which turns on a power-supply circuit 65 of the electric motor 10 and a power supply circuit 66 of the heating element 8. The circuit 65 turns on an n-p-n transistor 67 having its emitter connected to the contact 33 and its base and collector, which are coupled through a resistor 68, connected to a Zener diode 69 and the one arm of a diode bridge 70, respectively. The collector of the n-p-n transistor 67 is connected, through a capacitor 71, to a ground bus, and other arms of the diode bridge 70 are connected to a transformer 72. The circuit 66 turns on a diode bridge 73 having its arms connected to the transformer 72, the diode bridge 70 and, through a resistor 74, to the base of an n-p-n transistor 75 and a Zener diode 76. The junction point of one arm of the diode bridge 73, the collector of the n-p-n transistor 75 and the resistor 74 is connected, through a capacitor 77, to the ground bus. The emitter of the n-p-n transistor 76 and the collector thereof are connected to the base and collector of an n-p-n transistor 78, respectively. The base of the n-p-n transistor 78 is connected, through a resistor 79, to the ground bus. The circuit 62 for switching on the heating is built around a transistor 80 having its base connected, through a resistor 81, to the emitter of the n-p-n transistor 78 and the ground bus, its collector connected to the collectors of the n-p-n transistors 75, 78 and its emitter connected to one end of the heating element 8 by the flexible current lead 23.

The pulse generator 36 comprises an OR gate 82 having its inputs and output respectively connected to leads of a variable resistor 83 and to one input of another OR gate 84 having its second input connected to the noninverting output of the RS flip-flop 35 and its output, which is the output of the oscillator 36, connected, through a capacitor 85, to the inputs of the OR gate 82 and the counting T-input of the pulse counter 37.

The delay circuit 44 comprises series-connected resistors 86, 87 and NOR gate 88 whose output is the output of the delay circuit 44. The variable resistor 86 at the input of the delay circuit 44 is connected to the ground bus through a capacitor 89.

The switching circuits 58 and 63 are made identical and comprise one of n-p-n transistors 90 having their bases connected, through resistors 91, to the output of the respective OR gate 42, 51 and their emitters connected to the ground bus. The collectors of the n-p-n transistors 90 are respectively connected, through switching contacts, to one leads of sections 59', 59'' of the winding of the relay 59 having the other leads connected to the input of the power cut-in relay 64 comprising a winding 92 connected to diodes 93, 94 having their cathodes connected to the collectors of the n-p-n transistors 90. The relay 64 also comprises a speed control circuit built around an n-p-n transistor 95 having its base and collector connected to leads of a variable resistor 96 and the winding 92 and its emitter connected to a group 97 of switch contacts which are mechanically connected to a group 98 of the reverse switch 60. Contacts 99 and 100 of the switch 60 are connected to the negative terminal "−" of the electric motor 10, and contacts 101 and 102 are connected to the positive terminal "+" of the electric motor 10. The groups 97 and 98 of switch contacts of the switch 60 are operatively connected with the switch contacts of the relay 59, and the contact 98 of the switch 60 is electrically connected with a contact 103 of the relay 64 which also has contacts 104, 105 operatively connected with the winding 92.

The switching circuit 61 is made in the form of a relay having a winding 106 operatively connected with a group of contacts 107, 108, 109 for connecting to the other end of the heating element 8. The lead of the winding 106 is connected to the collector of an n-p-n transistor 110 having its base connected, through a resistor 111, to the output of the OR gate 43 and its emitter connected to the ground bus and the contact 107.

The device for coagulation of biological tissues functions as follows.

A desired coagulation depth, i.e. depth "l" to which the heating element 8 (FIG. 1) is introduced in the eye cornea, is determined beforehand using the results of medical examination of a patient.

Before the operation starts, the dial gage 18 is set to the depth "l" of the heating element 8 (FIG. 1) by turning the head 25 (FIG. 2) of the hollow fine adjustment screw 24 and using the scale 28 and indicator mark 29. When the head 25 (FIG. 2) of the hollow fine adjustment screw 24 is turned, the end of the screw really moves along the shaft 11 to the desired depth "l" which is proportional to the distance "$l_1$" (FIG. 1) between the wall of the casing 1 and the end of the hollow fine adjustment screw 24 (FIG. 2). The device is then brought to the eye cornea, and the rigid ring 20 (FIG. 1) of the limit stop of the heating element 8 is lightly pressed against the eye cornea.

The contacts 33, 34 (FIG. 5) are closed to turn on the flip-flop 35 which supplies a signal authorizing the work of the pulse generator 36 and simultaneously cancels the inhibiting signal at the R-input of the pulse counter 37. With the arrival of the first pulse at the pulse counter 37, "1" signal appears at its output 38 and is fed, through the OR gate 42, to the input of the switching circuit 58 which energizes the reverse relay 59 and power cut-in relay 64. Switch contacts of the reverse relay 59 determine the rotation direction of the shaft 11 (FIG. 1) of the electric motor 10 by connecting to the respective section 59' or 59'' of the winding. The contacts 104, 103 (FIG. 6) of the power cut-in relay 64 connect the power supply unit 22 to the electric motor 10. The electric motor 10 starts to rotate the shaft 11 (FIG. 1), and the hollow rod 6 connected to the shaft 11 by the connecting member 14 moves forward along its longitudinal axis as shown by arrow "a". The electric motor 10 will be switched on during four clock periods of the pulse counter 37 (FIG. 5), the heating element 8 being energized at the second clock period when there is a signal at the outputs 39, 40, 41 and when the following circuit is formed: the outputs 39, 40, 41 of the pulse counter 37, the input of the OR gate 43, the switching circuit 61, the heating element 8, the heating cut-in circuit 62, the power supply unit 22.

The duration of pulses produced by the generator 36 is chosen so that the time necessary for the hollow rod 6 to travel through the entire length of its working stroke is equal to three clock periods. In the interval between the third and forth pulses the electric motor 10 continues to rotate the helical shaft 11 (FIG. 1) making the resilient fork 31 (FIG. 2) slide over the helical line of the shaft 11 at a point where the elastic fork 31 bears against the end of the hollow fine adjustment screw 24. Microvibrations of the working end 9 (FIG. 1) of the heating element 8 occur resulting from the fact that the thread of the shaft 11 (FIG. 2) moves apart the prongs of the elastic fork 31, and they move backwards at one pitch. In this position, the heating element 8 (FIG. 1) enters the eye cornea through the rigid ring 20 while vibrating which eliminates deformation of the thin working end 9 of the heating element 8. When "1" pulse appears at the output 46 (FIG. 5) of the counter 37, there is no "1" signal at its output 38 resulting in that the electric motor is switched off through the following circuit: the OR gate 42, the switching circuit 58, the reverse relay 59, the power cut-in relay 64, the switch 60, the electric motor 10. The heating element 8 remains switched on through the following circuit: the OR gate 43, the switching circuit 61, the heating element 8, the heating circuit 62. The time-delay circuit 44 is switched on, and, when the time delay runs out, the AND gate 45 turns on. Being turned on, the AND gate 45 supplied a signal inhibiting counting to the inhibiting input of the pulse counter 37 thus ensuring the cessation of counting. At this moment, the charging of the capacitor 89 (FIG. 6) of the time-delay circuit 44 starts. The charging time of the capacitor 89 is determined by the elements of the circuit (resistors 86, 87) tuned by the operator. This time is the time of treatment of the cornea with the heating element 8. When the operation voltage of the NOR gate 88 is reached across the capacitor 89 of the time-delay circuit 44, the NOR gate 88 operates to cancel, through the AND gate 45, the signal inhibiting counting applied to the inhibiting input of the pulse counter 37.

Signal "1" appears at the output 47 of the pulse counter 37 and disappears from the outputs 39, 40, 41 thereof resulting in switching off the heating element 8 through the following circuit: the OR gate 43, the switching circuit 61, the heating element 8. Signal "1" appears at the output of the AND gate 51 to switch on, through the switching circuit 63, the reverse relay 59 and the power cut-in relay 64, the electric motor 10 (FIG. 1) which will have the direction of rotation of the shaft 11 opposite to the previous one, i.e. backwards (arrow "b"). During the sixth, seventh, eighth, tenth clock periods, the hollow rod 6 moves backwards and takes the initial position. After "1" signal has appeared at the output 52 of the pulse counter 37 which signal closes the contacts 53, 54, 55, 57 to drive the flip-flop 35 into its initial state, the operation cycle of the device is completed. To set the automatic mode of the device, it is sufficient to open the contacts 55, 57 of the mode switch member 56.

The use of the device according to the invention makes it possible to increase the accuracy of operation approximately two fold by ensuring precisely measured treatment. Such improvement of accuracy is obtained due to extending the working end 9 of the heating element 8 to a preset calculated depth, reciprocations of the heating element 8 with respect to the casing 1 and its stable position achieved by means of the limit stop 17 of the hollow rod 6 and the limit stop of the heating element 8. Operational and post operational implications are reduced by 35% which is the result of automatic control of the treatment time and heating temperature of the heating element 8 since overcauterization of tissues is eliminated.

Despite the device is equipped with the electric motor 10, the limit stop 17 of the hollow rod 6, the limit stop of the heating element 8 secured to the hollow rod 6, its dimensions are still modest (length ~120 mm with the diameter of the casing 1 at the place where the electric motor 10 is disposed $\phi \approx 25$ mm) and it is not heavy (not more than 70 g).

What we claim is:

1. A device for coagulation of biological tissue which is the object of treatment, comprising:
    a casing having a working butt end for facing an object of treatment having biological tissue;
    a heating element accommodated in said casing and having a working end protruding outside said working butt end of said casing for introduction into and acting on said biological tissue;
    a hollow rod having two butt ends mounted for reciprocation in said casing;
    said heating element being rigidly secured to one of said butt ends of said hollow rod;
    an electric motor accommodated in said casing;
    a shaft operatively connected with said electric motor and accommodated in said casing;
    a connecting member secured to the other of said butt ends of said hollow rod and operatively connecting said hollow rod to said shaft;
    a first limit stop having a dial gage, said first limit stop being mounted on said casing for engaging said connecting member in order to provide a predetermined depth of said introduction of said working end of said heating element;
    a second limit stop having one end rigidly secured to said casing and another end coaxially surrounding said working end of said heating element for stabilizing said introduction depth of said working end of said heating element;
    an automatic control unit connected to said electric motor and heating element for automatically controlling the heating temperature of said heating element and the time of said acting on said biological tissue, said automatic control unit having inputs and outputs;
    a power supply unit for supplying power to said electric motor for moving said shaft and to said heating element for its heating, the power supply unit having outputs connected to said inputs of said automatic control unit, said outputs of said automatic control unit being connected to an input of said power supply unit, said electric motor and said heating element.

2. A device according to claim 1, wherein the second stop is in the form of a cantilever having one end thereof rigidly secured to said working butt end of the casing and the other end adapted to face the object of treatment; and wherein
    a rigid ring is secured to said other end of said cantilever coaxially with said working end of the heating element;
    said working end of the heating element being in the form of a conical pointed member.

3. A device according to claim 1, wherein:
    said casing comprises a threaded hole in a wall coaxially with said shaft;
    said dial gage of said first limit stop comprises a hollow fine adjustment screw mounted coaxially with said shaft in said threaded hole;
    said hollow fine adjustment screw comprises a head disposed outside said casing and a butt end disposed on said shaft;
    said dial gage of first limit stop further comprising a scale provided on said head of said hollow fine adjustment screw and an indicator mark on said casing near said threaded hole for setting the end of said fine adjustment screw at a predetermined depth equal to said introduction depth of said working end;
    said shaft of the electric motor comprises a screw type; and
    said connecting member comprises a cantilever having one end of said cantilever rigidly secured to said other butt end of said hollow rod and another end of said cantilever in the form of a resilient fork bearing against said butt end of said hollow fine adjustment screw.

4. A device according to claim 2, wherein:
    said casing has a threaded hole in a wall coaxial with said shaft;
    said dial gage of said first limit stop comprises a hollow fine adjustment screw mounted coaxially with said shaft in said threaded hole;
    said hollow fine adjustment screw has a head disposed outside said casing and an end mounted on said shaft;
    a scale of said dial gage being provided on said head of said hollow fine adjustment screw and an indicator mark of said dial gage being on said casing near said threaded hole for setting the end of said fine adjustment screw at a predetermined depth equal to said introduction depth of said working end;
    said shaft of the electric motor is a screw type;
    said connecting member is a cantilever having one end of said cantilever rigidly secured to said other butt end of said hollow rod and another end of said cantilever in the form of a resilient fork engageable with said shaft for moving said hollow rod until said resilient fork bears against said end of said fine adjustment screw.

5. A device according to claim 1, wherein the unit for automatically controlling the heating temperature and time of treatment of biological tissue comprises:

an RS flip-flop having a reset R-input and S-input, a noninverting output and an inverting output;

a switch member connected to said S-input of said RS flip-flop for connecting to said power supply unit;

a pulse generator having its input connected to said noninverting output of said RS flip-flop;

a pulse counter having a counting input, a reset input, enabling signal input, two groups of outputs having equal number of outputs, a zero signal output and a treatment time signal output;

an output of said pulse generator and said inverting output of said RS flip-flop being connected to said counting input and said reset input of said pulse counter, respectively;

first, second and third OR gates having inputs the number of which corresponds to the pulse counter, each OR gate having one output;

said first OR gate having said inputs thereof connected to said outputs of the first group of the pulse counter for producing a signal enabling forward movement of the hollow rod;

said second OR gate having said inputs thereof connected to said outputs of the first group beginning from a second output and the treatment time signal output for producing a signal enabling heating of said heating element;

said third OR gate having said inputs thereof connected to said outputs of the second group of said pulse counter for producing a signal enabling backward movement of said hollow rod;

first and second switching circuits each having an input and an output;

a reverse relay having two inputs and two outputs;

said outputs of said first and third OR gates being connected, through said first and second switching circuits, to said inputs of said reverse relay for sending said signals enabling forward and backward movement of said hollow rod;

a power cut-in relay having one input connected to one said output of the reverse relay, another input designed to connect said electric motor to said power supply unit, and an output supplying a signal enabling connection to said power supply unit;

a reverse switch having two inputs connected to said outputs of the reverse relay and power cut-in relay for receiving said signal enabling forward and backward movement of the hollow rod and said signal enabling power supply switching on, and an output connected to said electric motor of the device;

a heating circuit of said heating element, having an input connected to said power supply unit of the device and an output connected to said heating element;

a third switching circuit having an input connected to said output of the second OR gate and designed to connect said heating element to said power supply unit through said heating circuit in case when there is said signal enabling heating at said output thereof;

a delay circuit having an input and an output;

an AND gate having two inputs and an output;

said inputs of said delay circuit and said AND gate being connected to said treatment time signal output of said pulse counter for initiating measurement of time during which the heating element acts upon the biological tissue;

said output of said delay circuit being connected to said second input of said AND gate for supplying a signal marking the end of the treatment time;

said output of said AND gate being connected to said enabling signal input of said pulse counter for supplying a signal initiating backward movement of the hollow rod after the time of treatment of the biological tissue has run out;

a mode switch member connected to said reset R-input of said RS flip-flop and to said switch member;

said zero signal output of said pulse counter being connected, through said switch member and said mode switch member, to said reset R-input of said RS flip-flop for beginning the next coagulation cycle.

* * * * *